(12) United States Patent
Liu et al.

(10) Patent No.: US 7,885,373 B2
(45) Date of Patent: Feb. 8, 2011

(54) SYSTEM AND METHOD FOR QUANTITATIVE IMAGING OF CHEMICAL COMPOSITION TO DECOMPOSE MULTIPLE MATERIALS

(75) Inventors: Xin Liu, Rochester, MN (US); Lifeng Yu, Rochester, MN (US); Cynthia H. McCollough, Byron, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 29 days.

(21) Appl. No.: 12/371,433

(22) Filed: Feb. 13, 2009

(65) Prior Publication Data

US 2009/0207967 A1 Aug. 20, 2009

Related U.S. Application Data

(60) Provisional application No. 61/029,132, filed on Feb. 15, 2008.

(51) Int. Cl.
*H05G 1/60* (2006.01)
(52) U.S. Cl. .......................................... 378/5
(58) Field of Classification Search .................. 378/4, 378/5, 19, 57, 64, 62
See application file for complete search history.

(56) References Cited

U.S. PATENT DOCUMENTS

| | | | |
|---|---|---|---|
| 4,029,963 | A | 6/1977 | Alvarez et al. |
| 5,235,628 | A | 8/1993 | Kalender |
| 6,987,833 | B2 | 1/2006 | Du et al. |
| 7,050,530 | B2 | 5/2006 | Heismann |
| 7,158,611 | B2 | 1/2007 | Heismann et al. |
| 2009/0129539 | A1* | 5/2009 | Licato et al. .................. 378/5 |

FOREIGN PATENT DOCUMENTS

| | | |
|---|---|---|
| DE | 10 2006 009222 A1 | 9/2007 |
| GB | 2 285 506 A | 7/1995 |

OTHER PUBLICATIONS

PCT/US2009/034111 Partial International Search Report; 2 pages.
Michael G J: Tissue Analysis Using Dual Energy CT; Australian Physical and Engineering Sciences In Medicine, Melbourne, vol. 15, No. 2, Jun. 1, 1992, pp. 75-87.
Liu et al: Quantitative Imaging Of Chemical Composition Using Dual-Energy Dual Source CT, Proceedings of SPIE, vol. 6913, Mar. 1, 2008, pp. 1-8.
Xin Liu et al, Quantitative Imaging of Chemical Composition Using Dual-Energy, Dual Source CT, Medical Imaging 2008, Physics of Medical Imaging, Proc. of SPIE vol. 6913 69134Z.
G.J. Michael, Tissue Analysis Using Dual Energy CT, Australasian Physical and Engineering Sciences in Medicine, Medicine, Melbourne, vol. 15, No. 2, Jun. 1, 1992.
PCT International Search Report and Written Opinion, 16 pages, PCT/US2009/034111, filing date Feb. 13, 2009.

* cited by examiner

*Primary Examiner*—Irakli Kiknadze
(74) *Attorney, Agent, or Firm*—Quarles & Brady LLP

(57) ABSTRACT

The present invention provides a material decomposition method capable of determining the distribution of density and constituent material concentration throughout an imaged object. The concentration, in the form of a mass fraction, mass percent, weight fraction, or weight percent, is determined from CT images acquired at different energy levels. The ratio of attenuation coefficients associated with one energy level to attenuation coefficients associated with another energy level is determined and used as an index in a lookup table to determine the concentration of a given material throughout the imaged object.

14 Claims, 3 Drawing Sheets

SYSTEM AND METHOD FOR QUANTITATIVE IMAGING OF CHEMICAL COMPOSITION TO DECOMPOSE MULTIPLE MATERIALS

CROSS-REFERENCE TO RELATED APPLICATIONS

This application is based on, incorporates herein by reference, and claims the benefit of U.S. Provisional Application 61/029,132, filed Feb. 15, 2008, and entitled "SYSTEM AND METHOD FOR QUANTITATIVE IMAGING OF CHEMICAL COMPOSITION TO DECOMPOSE MULTIPLE MATERIALS".

BACKGROUND OF THE INVENTION

The field of the invention is quantitative imaging and material decomposition. More particularly, the invention relates to a method for determining the mass fractions of constituent components of an object using CT imaging and a post-reconstruction material-basis model.

In a computed tomography system, an x-ray source projects a fan-shaped beam which is collimated to lie within an X-Y plane of a Cartesian coordinate system, termed the "imaging plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce the transmission profile at a particular view angle.

The source and detector array in a conventional CT system are rotated on a gantry within the imaging plane and around the object so that the angle at which the x-ray beam intersects the object constantly changes. A group of x-ray attenuation measurements from the detector array at a given angle is referred to as a "view", and a "scan" of the object comprises a set of views acquired at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique. This process converts the attenuation measurements from a scan into integers called "CT numbers" or "Hounsfield units", which are used to control the brightness of a corresponding pixel on a display.

Dual source CT systems have two separate x-ray sources and associated detector arrays, which rotate together in the gantry during a scan. The x-ray sources may be operated at different energy levels to acquire two image data sets from which a low energy and a high energy image may be reconstructed.

Quantitative imaging using CT systems has experienced tremendous growth in recent years, in terms of both the basic technology and new clinical applications. CT-based quantitative imaging exploits differences in x-ray attenuation between different materials. In CT images, because different materials cause different levels of x-ray scattering and absorption, proper calibration of image pixel values versus x-ray beam energy can be used to qualitatively and quantitatively evaluate an imaged object's material composition.

The degree to which a given material blocks x-ray transmission, is measured by an attenuation coefficient, which accounts for both energy absorption and the scattering of photons. Often, mass attenuation coefficients, which measure attenuation per unit mass, are utilized, because they do not change with the density of the material. Tabulated mass attenuation coefficients for different elements (Z=1~92) are readily available in the database of the National Institute of Standards and Technology (NIST). The NIST database also includes 48 compounds and mixtures, covering nearly all tissues found in the human body. The mass attenuation coefficient for compounds and mixtures having than more than one material is a summation of weighted mass attenuation coefficients of each constituent material, wherein the weighting factor is the mass fraction of each constituent material. Material decomposition techniques can be employed to calculate these mass fractions using known mass attenuation coefficients and dual energy CT measurements. In principle, this can only be done for objects having two constituent materials, as dual energy CT provides only two independent measurements.

Alternatively, material decomposition techniques can quantify an object under investigation by analyzing the physical mechanisms that cause attenuation. For the x-ray energies in the medical diagnostic range, the mechanisms responsible for material attenuation are the photoelectric effect and Compton scattering, which can be approximately modeled using effective atomic number, density, and x-ray energy information. Therefore, instead of obtaining the mass fraction of each material, the effective atomic number and density of the imaged object can be determined using a model of these two mechanisms and dual energy CT measurements.

In 1976, Alvarez and Macovski proposed a method to couple the attenuation coefficient model with CT measurements in order to determine the atomic number and density of a material. First, the attenuation coefficient ($\mu$( . . . )) is modeled as a linear combination of the photoelectric effect and Compton scattering, as follows:

$$\mu(x, y, E) = a_1(x, y)\frac{1}{E^3} + a_2(x, y)f_{KN}(E). \qquad \text{Eqn. 1}$$

In Eqn. 1, the photoelectric effect is inversely proportional to the energy level (E) cubed, and the Compton scattering is modeled by Klein-Nishina formula. The terms $a_1(x, y)$ and $a_2(x, y)$ are related to the atomic number and physical density of the materials under investigation. For a CT scan, this model is expressed as the following line integral:

$$\int \mu(x, y, E)ds = A_1 \frac{1}{E^3} + A_2 f_{KN}(E); \qquad \text{Eqn. 2}$$

where:

$$A_1 = \int a_1(x, y)ds; \qquad \text{Eqn. 3}$$

and $$A_2 = \int a_2(x, y)ds. \qquad \text{Eqn. 4}$$

From Eqn. 2, at least two equations are needed to obtain the single solution of the two unknowns. Because dual-energy CT images the object at two different energy levels, it satisfies this requirement and the equation can be written as follows:

$$I_i = \int S_i(E) e^{-\frac{A_1}{E^3} - A_2 f_{KN}(E)} dE \quad (i = 1, 2).\qquad\text{Eqn. 5}$$

However, it is very difficult to solve Eqn. 5 for $A_1$ and $A_2$. Alvarez and Macovski therefore used the following power series to approximate the integral equation:

$$\ln I_1 = b_0 + b_1 A_1 + b_2 A_2 + b_3 A_1^2 + b_4 A_2^2 + b_5 A_1 A_2 + b_6 A_1^3 + b_7 A_2^3 \qquad\text{Eqn. 6;}$$

and $$\ln I_2 = c_0 + c_1 A_1 + c_2 A_2 + c_3 A_1^2 + c_4 A_2^2 + c_5 A_1 A_2 + c_6 A_1^3 + c_7 A_2^3 \qquad\text{Eqn. 7.}$$

The sets of coefficients $\{b_i\}$ and $\{c_i\}$ are determined by calibrations. Once the $A_1$ and $A_2$ are solved using Eqn. 6 and 7, $a_1(x,y)$ and $a_2(x,y)$ can be reconstructed by one of the known reconstruction methods, such as filtered back projection.

This method, typically referred to as the basis-spectral method, was the first theoretical analysis on material-selective imaging using dual-energy CT. The drawback of the basis-spectral method is that it is not very accurate due to the intrinsic difficulty in modeling the photoelectric effect and Compton scattering, especially for discontinuous absorption edges. Although the basis-spectral method accounts for the photoelectric effect and Compton scattering by creating a photoelectric effect and Compton scattering map, this type of technique is more often used to give the object's effective atomic number and density.

In 1986, Kalender et al. proposed that any material's mass attenuation coefficient can be expressed as a linear combination of the coefficients of two so-called basis materials, as follows:

$$\left(\frac{\mu}{\rho}\right)(E) = a_1 \left(\frac{\mu}{\rho}\right)_1(E) + a_2 \left(\frac{\mu}{\rho}\right)_2(E). \qquad\text{Eqn. 8}$$

For a CT measurement, this is expressed using the following line integral:

$$\int \mu(x, y, E) ds = A_1 \left(\frac{\mu}{\rho}\right)_1(E) + A_2 \left(\frac{\mu}{\rho}\right)_2(E); \qquad\text{Eqn. 9}$$

where $$A_1 = \int \rho_1(x, y) ds; \qquad\text{Eqn. 10}$$

and $$A_2 = \int \rho_2(x, y) ds. \qquad\text{Eqn. 11}$$

This method is called the basis-material method. Similar to the basis-spectral method, dual-energy CT measurements are needed to solve the two unknowns $A_1$ and $A_2$. The assumption used with the basis-material method is that the attenuation coefficients of the two basis materials are known. From this assumption and the dual-energy CT measurements, the line integral equation can be written as follows:

$$I_i = \int S_i(E) e^{\left[-A_1 \left(\frac{\mu}{\rho}\right)_1(E) - A_2 \left(\frac{\mu}{\rho}\right)_2(E)\right]} dE. \qquad\text{Eqn. 12}$$

Instead of solving Eqn. 12 directly, the basis-material method uses a table lookup procedure to solve the equation and produce an output that can be interpreted as components in a two-dimensional vector space, wherein the basis materials define the basis vectors. As a result, the basis-material method using dual energy CT is more efficient and clinically practical than the above-described basis-spectral approach.

Although the basis-spectral and basis-material methods differ in their modeling of the attenuation coefficients, they both belong to the "pre-reconstruction" class of methods. That is, both methods are performed with "raw data," prior to image reconstruction. In contrast, a post-reconstruction method would be capable of analyzing reconstructed images directly.

In 2003, Heismann et al. proposed a post-reconstruction method for performing material decomposition using CT. Under the Heismann method, effective attenuation coefficient is first defined as follows:

$$\mu_{\mathit{eff}} = \lim_{d \to 0}\left[-\frac{1}{d}\ln\left(\frac{I}{I_0}\right)\right] = \lim_{d \to 0}\left[-\frac{1}{d}\ln\left(\frac{\int S(E)D(E)e^{-\mu(E)d}dE}{\int S(E)D(E)dE}\right)\right]. \qquad\text{Eqn. 13}$$

Then, as follows:

$$\mu_{\mathit{eff}} = \int w(E)\mu(E) dE; \qquad\text{Eqn. 14}$$

where $$w(E) = \frac{S(E)D(E)}{\int S(E)D(E) dE}. \qquad\text{Eqn. 15}$$

The effective attenuation coefficient ($\mu_{\mathit{eff}}$) is determined from the CT image data and $S(E)$ and $D(E)$ are the tube spectrum and detector sensitivity, respectively. Like the basis-spectral method, the Heismann method treats $\mu(E)$ as the following linear combination of the photoelectric effect and Compton scattering:

$$\begin{pmatrix} \mu_{\mathit{eff}1} \\ \mu_{\mathit{eff}2} \end{pmatrix} = \rho \begin{pmatrix} \int w_1(E)\left(\frac{\mu_{photo}}{\rho} + \frac{\mu_{Compton}}{\rho}\right) dE \\ \int w_2(E)\left(\frac{\mu_{photo}}{\rho} + \frac{\mu_{Compton}}{\rho}\right) dE \end{pmatrix}. \qquad\text{Eqn. 15}$$

Also similar to the basis-spectral method, the Heismann method models the photoelectric effect and Compton scattering as functions of atomic number and x-ray energy, respectively, as follows:

$$\frac{\mu_{photo}}{\rho} = \alpha \frac{Z^3}{E^3}; \qquad\text{Eqn. 16}$$

and $$\frac{\mu_{Compton}}{\rho} = \beta; \qquad\text{Eqn. 17}$$

where α and β are constants. Therefore, Heismann's post-reconstruction method determines an object's effective atomic number and density directly from CT images. The Heismann method, though able to utilize CT data post-reconstruction, shares many of the assumptions of the above-described pre-reconstruction spectral-basis method. As a result, the Heismann method shares many of the same shortcomings.

Heismann did not determine how to use the data in both the pre-reconstruction space and post-reconstruction space, how to solve the linear equations more accurately, and other measures, such as the beam hardening effect necessary to successfully implement such a method.

Accordingly, it would be desirable to have a system and method for performing two-material decomposition that is capable of providing the density and mass concentration of an object in post-reconstruction space.

SUMMARY OF THE INVENTION

The present invention overcomes the aforementioned drawbacks by providing a method for non-invasively measuring the quantity of a object's constituent materials in vivo. The method allows two-material decomposition and can provide images showing the distribution of density and constituent material concentration throughout the object. In contrast to prior methods, the present invention operates on reconstructed image data to provide improved efficiency and ease-of-implementation.

A method for determining a material decomposition using a CT system is disclosed that includes imaging an object with the CT system using at least two different energy levels to acquire CT data associated with each of the energy levels and reconstructing the acquired CT data associated with each of the energy levels to produce image data associated with each of the energy levels. The method also includes converting the image data associated with each of the energy levels to attenuation coefficients associated with each of the energy levels, calculating a ratio of the attenuation coefficients associated with one energy level to the attenuation coefficients associated with another energy level, and correlating the ratio calculated in step d) to indicate a concentration of a constituent material in the imaged object.

A method for determining a material decomposition using a CT system is disclosed that includes imaging an object with the CT system using at least two different energy levels to acquire CT data associated with each of the energy levels and reconstructing the acquired CT data associated with each of the energy levels to produce image data associated with each of the energy levels. The image data associated with each of the energy levels is converted to attenuation coefficients associated with each of the energy levels. The method also includes selecting corresponding portions of the image data associated with each of the energy levels, calculating a ratio of the attenuation coefficients associated with the selected corresponding portions of the image data, and determining, from the calculated ratio, a concentration of a constituent material in the portion of the imaged object corresponding to selected corresponding portions of the image data. Other portions of the image data associated with each of the energy levels are selected and for each the concentration of a constituent material is determined to create a representation of the object indicating the constituent material in the imaged object.

Various other features of the present invention will be made apparent from the following detailed description and the drawings.

DETAILED DESCRIPTION OF THE INVENTION

Figure 1:
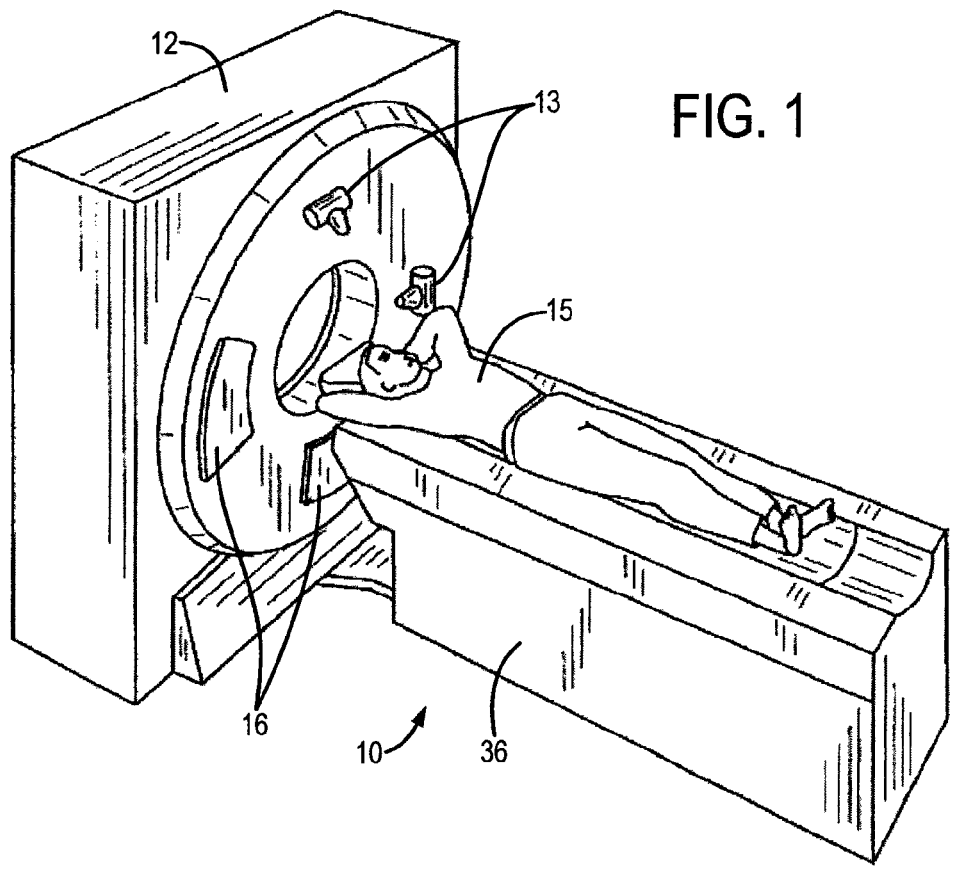
FIG. 1 is pictorial view of a CT imaging system in which the present invention may be employed.
Figure 2:
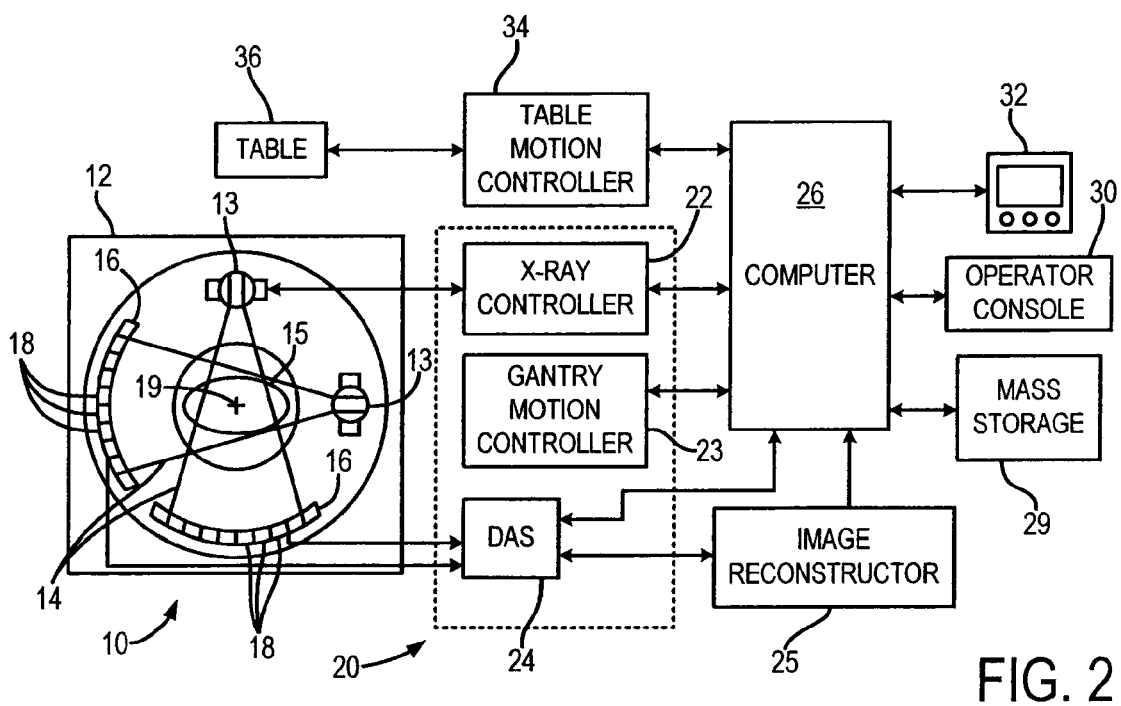
FIG. 2 is block schematic diagram of the CT imaging system.

With initial reference to FIGS. 1 and 2, a computed tomography (CT) imaging system 10 includes a gantry 12 representative of a "third generation" CT scanner. Gantry 12 has a pair of x-ray sources 13 that each project a fan beam or cone beam of x-rays 14 toward a detector array 16 on the opposite side of the gantry. The detector array 16 is formed by a number of detector elements 18 which together sense the projected x-rays that pass through a medical patient 15. Each detector element 18 produces an electrical signal that represents the intensity of an impinging x-ray beam and hence the attenuation of the beam as it passes through the patient. During a scan to acquire x-ray projection data, the gantry 12 and the components mounted thereon rotate about a center of rotation 19 located within the patient 15 to acquire attenuation data for each of the two x-ray sources.

The rotation of the gantry and the operation of the x-ray sources 13 are governed by a control mechanism 20 of the CT system. The control mechanism 20 includes an x-ray controller 22 that provides power and timing signals to the x-ray sources 13 and a gantry motor controller 23 that controls the rotational speed and position of the gantry 12. A data acquisition system (DAS) 24 in the control mechanism 20 samples analog data from detector elements 18 and converts the data to digital signals for subsequent processing. An image reconstructor 25, receives sampled and digitized x-ray data from the DAS 24 and performs high speed image reconstruction. The reconstructed image is applied as an input to a computer 26 which stores the image in a mass storage device 29.

The computer 26 also receives commands and scanning parameters from an operator via console 30 that has a keyboard. An associated display 32 allows the operator to observe the reconstructed image and other data from the computer 26. The operator supplied commands and parameters are used by the computer 26 to provide control signals and information to the DAS 24, the x-ray controller 22 and the gantry motor controller 23. In addition, computer 26 operates a table motor controller 34 which controls a motorized table 36 to position the patient 15 in the gantry 12.

Figure 3:
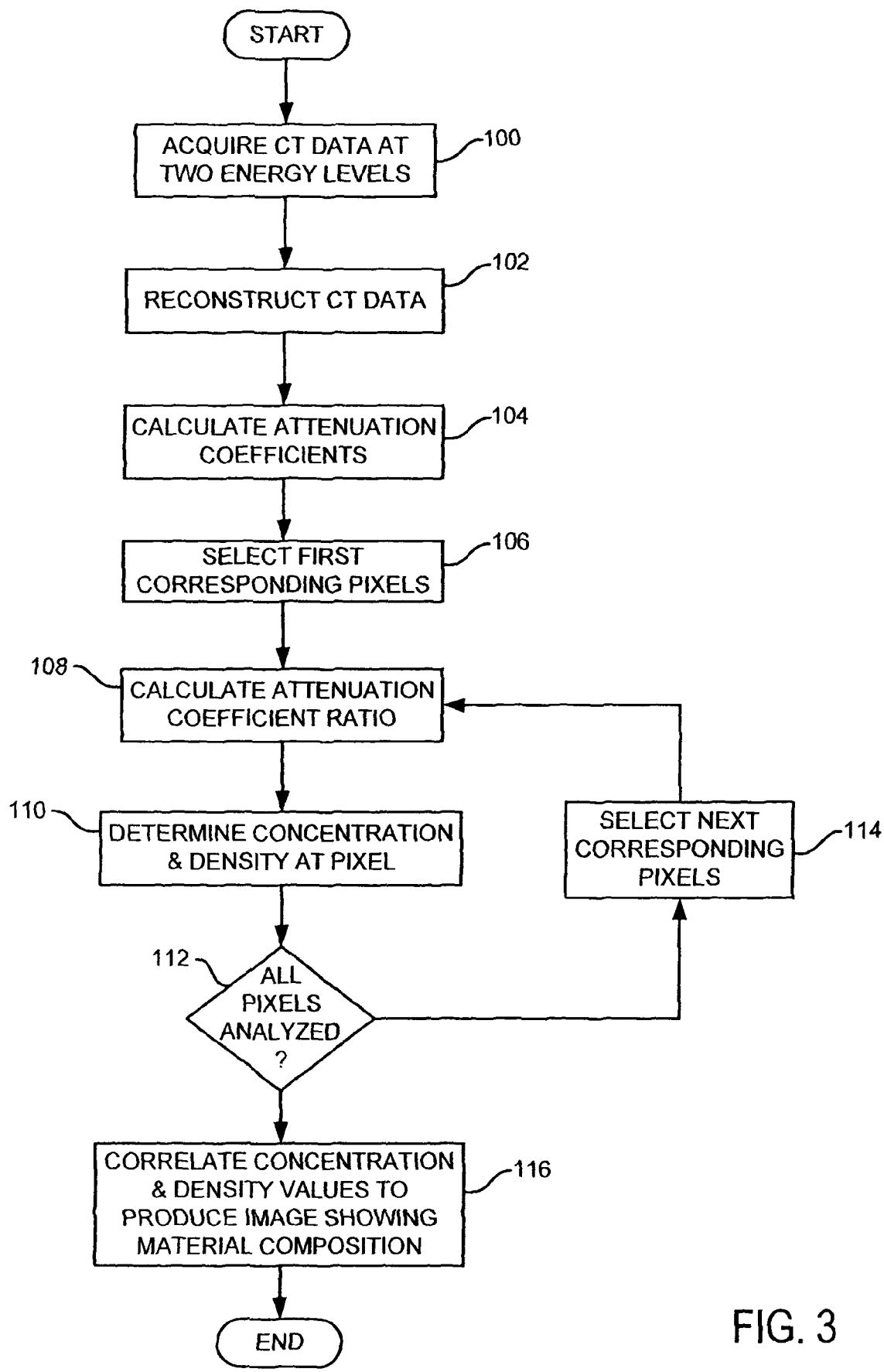
FIG. 3 is a flowchart setting forth the steps of performing material decomposition in accordance with the present invention.

Referring now to FIG. 3, the above-described CT system may be employed to perform post-reconstruction two-material decomposition and provide density and concentration information for the constituent materials of an imaged object. A method for performing material decomposition in accordance with the present invention begins at process block 100 with the acquisition of CT data at two different energy spectra. For example, a dual energy CT system may be used to acquire CT data at 80 kVp and 120 kVp. At process block 102, the acquired CT data is reconstructed to produce CT images for each prescribed energy level, for example, filtered back-projection may be employed to produce registered CT images for the 80 kVp scan and the 120 kVp scan. Subsequently, at process block 104, the CT images are processed so that the CT number in Hounsfield Units (HU) at each pixel is converted to an attenuation coefficient value.

As addressed above, the total mass attenuation coefficient of an object containing two constituent materials is the weighted sum of the two constituent material's mass attenuation coefficients. If the types of the two materials are known, such as is generally true or can be assumed when imaging the human body, the process can then focus on determining the concentration of each material in the imaged object. Accordingly, the problem can be modeled as follows:

$$\left(\frac{\mu}{\rho}\right)(E) = a\left(\frac{\mu}{\rho}(E)\right)_1 = (1-a)\left(\frac{\mu}{\rho}(E)\right)_2; \quad \text{Eqn. 18}$$

where a is the weight percent of the first material within the object and (1−a) is the weight percent of the second material. Then, in the image space, this can be rewritten as follows:

$$\begin{pmatrix}\mu_{eff1}\\\mu_{eff2}\end{pmatrix} = \rho_{eff}\begin{pmatrix}\int w_1(E)\left[a\left(\frac{\mu}{\rho}(E)\right)_1 + (1-a)\left(\frac{\mu}{\rho}(E)\right)_2\right]dE\\\int w_2(E)\left[a\left(\frac{\mu}{\rho}(E)\right)_2 + (1-a)\left(\frac{\mu}{\rho}(E)\right)_2\right]dE\end{pmatrix}. \quad \text{Eqn. 19}$$

Figure 4:
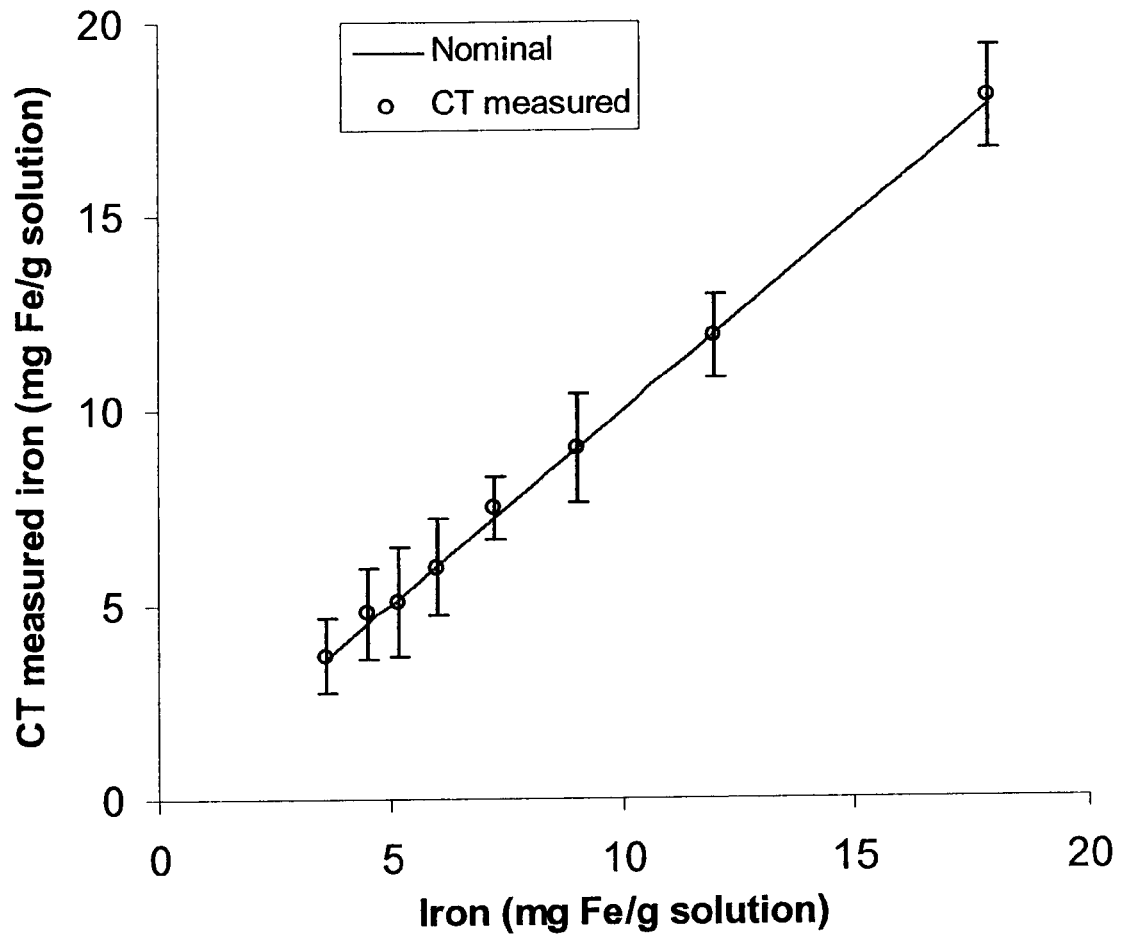
FIG. 4 is an example a lookup table for determining iron concentration in accordance with the present invention.

Referring now to FIGS. 3 and 4, at process block 106, corresponding pixels in the CT images associated with each energy level are selected and, at process block 108, the ratio of attenuation coefficients at these pixels is calculated, that is, the ratio of $\mu_{eff1}$ to $\mu_{eff2}$. For example, the ratio of pixel $(i_1, j_1)$ from an 80 kVp scan to pixel $(i_1, j_1)$ from a 120 kVp scan may be calculated. At process block 110, material concentrations, a and (1−a), and effective density, $\rho_{eff}$, are determined using a lookup table that relates the material concentration a to the ratio of $\mu_{eff1}$ to $\mu_{eff2}$. Generally, these tables express the material concentration a as a one-dimensional monotonic function of the ratio of attenuation coefficients. If, at decision block 112, all corresponding pixels in the CT images have not been analyzed, then a next set of corresponding pixels is selected at process block 114 and the material decomposition steps of process blocks 108 and 110 are repeated. When all pixels have been analyzed, at process block 116, the determined constituent material concentrations and densities are correlated to image pixels to produce a material composition image showing the distribution of constituent material concentration and density in the imaged object.

For example, in the above-noted dual energy CT scan, the ratio of an attenuation coefficient at a given pixel in the 80 kVp scan data to an attenuation coefficient at the corresponding pixel in the 120 kVp scan data may be determined. Then, using the iron concentration lookup table of FIG. 4, this ratio may then be employed to determine the concentration of iron in the imaged object. This process may be repeated to determine the concentration of iron at the spatial locations represented by each set of corresponding pixels to produce an image showing the distribution of iron in a subject. Such an image could allow an in vivo assessment of iron overload, such as occurs in hemochromatosis.

It should be noted that the material concentration a can be a mass fraction, mass percent, weight fraction, weight percent, or any other appropriate measure of concentration. It should also be noted that this method can be utilized with dual-energy, single-source CT systems; dual-source, dual-energy CT systems; or any other CT system capable of acquiring multi-energy data. For example, so-called "photon counting" and "energy discriminating" CT systems can also be employed. In such systems, one spectrum is measured and divided into two energy bands.

The present invention has been described in accordance with the embodiments shown, and one of ordinary skill in the art will readily recognize that there could be variations to the embodiments, and any variations would be within the spirit and scope of the present invention. Accordingly, many modifications may be made by one of ordinary skill in the art without departing from the spirit and scope of the appended claims.

The invention claimed is:

1. A method for determining a material decomposition using a CT system, the steps comprising:
   a) imaging an object with the CT system using at least two different energy levels to acquire CT data associated with each of the energy levels;
   b) reconstructing the acquired CT data associated with each of the energy levels to produce image data associated with each of the energy levels;
   c) converting the image data associated with each of the energy levels to attenuation coefficients associated with each of the energy levels;
   d) calculating a ratio of the attenuation coefficients associated with one energy level to the attenuation coefficients associated with another energy level;
   e) correlating the ratio calculated in step d) to indicate a concentration of a constituent material in the imaged object and
   f) correlating the concentration of a constituent material to the image data to create an image showing a distribution of the concentrations of the constituent material.

2. The method as recited in claim 1 wherein the CT system is at least one of a dual-energy, single-source CT system; a dual-source, dual-energy CT system; a photon counting CT system; and an energy discriminating CT system.

3. The method as recited in claim 1 wherein step e) further includes comparing the ratio calculated in step d) to a lookup table relating attenuation coefficient ratios to the concentration of the constituent material.

4. The method as recited in claim 3 wherein the concentration is at least one of a mass fraction, mass percent, weight fraction, and weight percent.

5. The method as recited in claim 1 wherein step e) includes calculating an effective density.

6. The method as recited in claim 5 wherein concentration is determined for two constituent materials in the imaged object.

7. The method as recited in claim 6 wherein step c) further includes expressing the attenuation coefficients associated with each energy level as a weighted sum of the attenuation coefficients of the constituent materials.

8. A method for determining a material decomposition using a CT system, the steps comprising:
   a) imaging an object with the CT system using at least two different energy levels to acquire CT data associated with each of the energy levels;
   b) reconstructing the acquired CT data associated with each of the energy levels to produce image data associated with each of the energy levels;
   c) converting the image data associated with each of the energy levels to attenuation coefficients associated with each of the energy levels;
   d) selecting corresponding portions of the image data associated with each of the energy levels;

e) calculating a ratio of the attenuation coefficients associated with the selected corresponding portions of the image data;

f) determining from the ratio calculated in step e) a concentration of a constituent material in the portion of the imaged object corresponding to selected corresponding portions of the image data;

g) repeating steps d) through f) to determine a concentration of a constituent material in the imaged object; and h) creating a representation of the object indicating the constituent material in the imaged object.

9. The method as recited in claim 8 wherein the CT system is at least one of a dual-energy, single-source CT system and a dual-source, dual-energy CT system.

10. The method as recited in claim 8 wherein step f) further includes comparing the ratio calculated in step e) to a lookup table relating attenuation coefficient ratios to the concentration of the constituent material.

11. The method as recited in claim 10 wherein the concentration is at least one of a mass fraction, mass percent, weight fraction, and weight percent.

12. The method as recited in claim 8 wherein step f) includes calculating an effective density.

13. The method as recited in claim 12 wherein concentration is determined for two constituent materials in the selected corresponding portions of the image data.

14. The method as recited in claim 13 wherein step c) further includes expressing the attenuation coefficients associated with each energy level as a weighted sum of the attenuation coefficients of the constituent materials.

* * * * *